(12) United States Patent
Femat Flores et al.

(10) Patent No.: US 10,280,366 B2
(45) Date of Patent: May 7, 2019

(54) WHITE LIGHT EMITTING MATERIAL AND METHOD OF PREPARATION AND USES THEREOF (71) Applicants: Instituto Potosino de Investigación Cientifica y Tecnológica A.C., San Luis Potosí (MX); UNIVERSIDAD NACIONAL AUTONOMA DE MEXICO, México, D.F. (MX)

(72) Inventors: Alejando Ricardo Femat Flores, San Luis Potosí (MX); David Rios Jara, San Luis Potosí (MX); Larissa Alexandrova, México, D.F. (MX); César Augusto Fernández Gijón, D.F. (MX); Guillermo Santana Rodriguez, Mexico City (MX)

(73) Assignees: Instituto Potosino DE Investigación Cientiffica y Technológica A.C., San Luis Potosi (MX); UNIVERSIDAD NACIONAL AUTONOMA de Mexico, Mexico City (MX)

( * ) Notice: Subject to any disclaimer, the term of this patent is extended or adjusted under 35 U.S.C. 154(b) by 137 days.

(21) Appl. No.: 15/188,142

(22) Filed: Jun. 21, 2016

(65) Prior Publication Data
US 2016/0376500 A1    Dec. 29, 2016

Related U.S. Application Data (60) Provisional application No. 62/183,325, filed on Jun. 23, 2015.

(51) Int. Cl.
*C07D 487/06* (2006.01)
*C09K 11/06* (2006.01)
*C08F 220/14* (2006.01)

(52) U.S. Cl.
CPC ............ *C09K 11/06* (2013.01); *C07D 487/06* (2013.01); *C08F 220/14* (2013.01); *C09K 2211/1048* (2013.01); *C09K 2211/1466* (2013.01); *Y02B 20/181* (2013.01)

(58) Field of Classification Search
CPC .................................................. C07D 487/06
USPC ......................................................... 544/248
See application file for complete search history.

(56) References Cited

U.S. PATENT DOCUMENTS

| 5,466,805 A | 11/1995 | Roschger |
| 5,530,130 A | 6/1996 | Roschger et al. |
| 5,830,931 A | 11/1998 | Pelster et al. |
| 7,662,308 B2 | 2/2010 | Jeganathan et al. |
| 2012/0157586 A1 | 6/2012 | Dern |

FOREIGN PATENT DOCUMENTS

| EP | 828986 | 3/1998 |
| EP | 1245645 | 10/2002 |
| EP | 1765268 | 3/2007 |
| JP | 2012172070 A | 9/2012 |
| JP | 2013203931 A | 10/2013 |
| JP | 2014214244 A | 11/2014 |
| WO | WO2008092771 A1 | 8/2008 |
| WO | WO2011054731 A1 | 5/2011 |

OTHER PUBLICATIONS

Mobinikhaledi A.; Amrollahi M.A.; Foroughifar N.; Jirandehi H. F. Asian J. Chem. 2005, 17(4), 2411-2414.
Vargas Alfredo N.; Likhatchev D.; Barrientes Ramirez S.; Revilla Vazquez J.; Cedillo Valverde G.; Alexandrova L. Polymer. 2008, 49, 3654-62.
Hartford S.L.; Subramanian S.; Parker J.A. J. Polym. Sci.: Polym. Chem. Ed.1978, 16, 137-53.
Otsu T.; Yang J-Z. Polym. Int. 1991, 25, 245-15.
Watanabe H.; Matsumoto A.; Otsu T. J. Polym. Sci.: Part A: Polym. Chem. 1994, 32, 2073-83.
Likhatchev D.; Valle L.; Canseco M.; Gaviño R.; Martinez-Richa A.; Alexandrova L.; Vera-Graziano R. J. Appl. Polym. Sci. 1998, 67, 609-619.
Likhatchev D.; Granados-Focil S.; Gaviño R.; Alexandrova L. High Perform. Polym. 1999, 11, 405-415.
Salcedo R.; Valle L.; Alexandrova L.; Likhatchev D. J. Molec. Structure (Theochem). 1999, 463, 231-235.
Dinand. E.; Zloh M.; Brocchini S. Aust. J. Chem. 2002, 55(6-7), 467-74.
Guzman-Lucero D.; Likhatchev D. Polym. Bull. 2002, 48, 261-269.

*Primary Examiner* — Jeffrey H Murray
(74) *Attorney, Agent, or Firm* — Defillo & Associates; Evelyn A Defillo (57) ABSTRACT The instant invention is related with new perimidine derivatives synthesized via direct condensation between naphthalene-1,8-diamine and itaconic or citraconic anhydrides at low temperature. The targeting itaco-perinone (IP) molecule formed via double low temperature cyclization has fluorescence properties emitting white light intensively. Besides, 9-methylene-8H-pyrrolo[1,2-a]perimidin-10(9H)-one is copolymerizable with several kind of organic monomer compounds via free radical mechanism maintaining the ability to emit white light even within the polymer film.

7 Claims, 3 Drawing Sheets

WHITE LIGHT EMITTING MATERIAL AND METHOD OF PREPARATION AND USES THEREOF

CROSS-REFERENCE TO RELATED APPLICATIONS

This application claims the benefit of priority to U.S. Provisional Application No. 62/183,325, filed Jun. 23, 2015, the contents of which are incorporated herein by reference.

FIELD OF THE INVENTION

The instant invention is related with new perimidine derivatives synthesized via direct condensation between naphthalene-1,8-diamine and itaconic or citraconic anhydrides at low temperature. The targeting itaco-perinone (IP) molecule formed via double low temperature cyclization has fluorescence properties emitting white light intensively. Besides, 9-methylene-8H-pyrrolo[1,2-a]perimidin-10(9H)-one is copolymerizable with several kind of organic monomer compounds via free radical mechanism maintaining the ability to emit white light even within the polymer film.

BACKGROUND OF THE INVENTION

Pyrroloperimidines or perinones are fused heterocyclic compounds and generally known as basis for various dyes and pigments recommended for wide range of industrial plastics, and synthetic and natural fibers. (e.g. JP 2014214244 A, JP 2013203931 A, JP 2012172070 A, US 20120157586 A1, WO 2008092771 A1) Owing to the highly conjugated structures, these compounds have excellent resistance to heat and light and maintain the brightness of color even under plastic processing or long term sun exposure. Some of them, except bright color, show photoluminescence in short wavelength ranges. (US 2014345195 A1)

The vast majority of the methods reported for synthesis of the perinones are based on condensation of naphthalene-1,8-diamine (NDA) with carboxylic acids or the corresponding anhydrides by refluxing in high boiling solvents or in aggressive acidic media. (e.g. U.S. Pat. No. 5,530,130, U.S. Pat. No. 5,466,805, EP 828,986, U.S. Pat. No. 5,830,931, EP 1,245,645). The reaction proceeds by double cyclization via monoacyl intermediate 1 and the formation of 2-substituted H-perimidine as the most probable product of the first cyclization step.

The arising interest in the perimidine-like structures in the last years has been owned to their possible biological activities. Such various 1- and 2-substituted perimidines have been proposed as anti-fungal, anti-ulcer and anti-tumor agents.

Now then, several documents describe fluorescent dyeing compounds, but not related with the structure of the instant invention's compounds. For example, WO2011054731A1 refers to fluorescent dyes with a POSS domain covalently attached to an organic chromophore domain.

EP1765268 A1, refer to perilene fluorescent compounds useful for hair treatments. Other fluorescent compounds for hair dyes are described in U.S. Pat. No. 7,662,308B2. As far as we know, no perinone compounds even with similar structures have been described as white light emitting molecules in a wide light spectrum.

The 2-substituted perimidines are formed by condensation of NDA not only with acids and their derivatives (anhydrides, acyl chlorides) but with other compounds containing carbonyl group as aldehydes or ketones.

The ring-closure reaction with anhydrides is considered as the best synthetic route because of various reasons: firstly this method allows formation of the product directly in one step in contrast to the reaction with aldehydes or ketones and secondly resulted in the highest yield and less contaminated product in comparison to the reactions with carboxylic acids and acyl chlorides, correspondingly. However, frequently reflux in acetic or trifluoroacetic anhydrides for several hours is needed for the cyclization. Recently, the microwave-assisted synthesis has been developed, which allowed to decrease the reaction time and simultaneously increase the yields with both aliphatic and aromatic acids using high power oven (900 W) (Mobinikhaledi A.; Amrollahi M. A.; Foroughifar N.; Jirandehi H. F. Asian J. Chem. 2005, 17(4), 2411-2414).

SUMMARY OF THE INVENTION

The instant invention is related with a luminescent perinone compound of formula:

comprising the following spectroscopic parameters: $^1$H NMR (500 MHz, CDCl$_3$, δ ppm): 3.55 (t, J=2.5 Hz, 2H)(8), 5.70 (t, J=2.3 Hz, 1H)(9a), 6.39 (t, J=2.7 Hz, 1H)(9a), 7.04 (dd, J=7.1, 1.1 Hz, 1H)(6), 7.32 (td, J=8.1, 2.3 Hz, 2H)(2 and 5), 7.36 (dd, J=8.3, 1.0 Hz, 1H)(4), 7.44 (dd, J=8.3, 0.6 Hz, 1H)(3), 8.31 (dd, J=7.7, 0.8 Hz, 1H)(1). $^{13}$C NMR (126 MHz, CDCl$_3$ δ, ppm): 166.09 (quart)(10), 153.53 (quart)(7a), 139.43 (quart)(6a), 134.17 (quart)(3a), 133.06 (quart)(9), 131.80 (quart)(11a), 128.07 (tert)(5), 127.26 (tert)(2), 123.91 (tert)(3), 123.56 (tert)(4), 120.87 (sec)(9a), 119.84 (quart)(3a'), 118.79 (tert)(6), 109.77 (tert)(1), 31.15 (sec)(8); MS (DART) m/z=234, preferably the compound is 9-methylene-8H-pyrrolo[1,2-a]perimidin-10(9H)-one In a further embodiment, the invention relates to a white luminescent material comprising a compound of formula and an organic monomer, wherein the preferred compound is 9-methylene-8H-pyrrolo[1,2-a]perimidin-10(9H)-one, and the organic monomer comprises styrene, vinyl, acrylate and/or methacrylate. In a most preferred embodiment said 9-methylene-8H-pyrrolo[1,2-a]perimidin-10(9H)-one and said styrene, vinyl, acrylate and/or methacrylate conform a luminescent polymer.

Is an additional embodiment of the invention a process for preparing a compound of formula comprising the steps of: reacting naphthalene-1,8-diamine with itaconic acid and citraconic anhydride. Said process further comprising reacting the itaconic acid and the citraconic anhydride with polar compounds comprising tetrahydrofurane, chloroform, ethylene acetic, N-methyl-2-pyrrolidone and dimethylformamide; wherein the mixture is filtered and further precipitated. In a further step the precipitated further reacts with organic solvents, wherein said organic solvents are tetrahydrofurane, acetic anhydride and sodium acetate.

DETAILED DESCRIPTION OF THE INVENTION

The instant invention relates to research concerning cyclization between acid anhydrides and aromatic diamines, such as o-phenylene diamine and NDA, resulted in synthesis of fused pyrrone and perinone frameworks respectively at room temperature. (Vargas Alfredo N.; Likhatchev D.; Barrientes Ramirez S.; Revilla Vazquez J.; Cedillo Valverde G.; Alexandrova L. Polymer. 2008, 49, 3654-62) The route to perinones was particularly effective with high yield products. Thus, using maleic, succinic, cis-1,2,3,6-tetrahydrophtalic and 1,2-cyclohexandicarboxylic anhydrides the corresponding perinones (MP, SP, THPP and HHPP) have been readily obtained. However, only citraco-perinones (CPs), two isomeric forms, were formed from itaconic anhydride (IA) because of a fast itaco-citraco rearrangement under the cyclization conditions, no itaco-perinone (IP) has been obtained so far. Reactivity of the perinones in the copolymerizations depended strongly on the position of the double bond and less conjugated THPP was easier to incorporate into the polymer chain than more conjugated MP and CPs. Then, it could be assumed that 9-methylene-8H-pyrrolo[1,2-a]perimidin-10(9H)-one with the reactive carbon-carbon double bond located outside the five-membered cycle should be much more active in the addition polymerization as it has been demonstrated for various itaconic derivatives in comparison to the maleic ones. Besides, since the itaco-citraco isomerization occurs at significant rate above 50° C., 9-methylene-8H-pyrrolo[1,2-a]perimidin-10(9H)-one could not be obtained using high temperature methods. ((a) Hartford S. L.; Subramanian S.; Parker J. A. J. Polym. Sci.: Polym. Chem. Ed. 1978, 16, 137-53; (b) Otsu T.; Yang J-Z. Polym. Int. 1991, 25, 245-15; (c) Watanabe H.; Matsumoto A.; Otsu T. J. Polym. Sci.: Part A: Polym. Chem. 1994, 32, 2073-83; (d) Solanki A.; Choudhary V.; Varma I. K. J. Appl. Polym. Sci. 2002, 84, 2277-82. (e) Solanki A.; Chouldhary V.; Varma K. Polym. Int. 2002, 51, 493-501; (f) Galanty A. V. J. Polym. Sci.: Polym. Chem. Ed. 1981, 19, 2243-53; (g) Dinand. E.; Zloh M.; Brocchini S. Aust. J. Chem. 2002, 55(6-7), 467-74.)

Therefore, the instant invention is related with a novel synthesis of a compound of formula:

preferably 9-methylene-8H-pyrrolo[1,2-a]perimidin-10(9H)-one (IP) with several organic compounds, but not limited to trifluoroacetic anhydride, thionyl chloride, polyphosphoric acid, phosphorous pentoxide, phosphoryl chloride, N,N-dicyclohexylcarbodiimide, on the cyclizations and formation of perimidine skeletons. Said novel synthesis method allows a compound with wide wavelength range, thus producing a white luminescent compound useful for multiple applications.

In previous publications the majority of the synthesized perinones were obtained via single-stage method and the intermediate compounds were not fully characterized, since a mixture of by-products or final products were obtained. However, according to the numerous literature data it was proposed a formation of the corresponding monoacylated intermediates as principal products of the reactions between NDA and the anhydrides taken in equimolar amounts before an addition of the dehydrating agent. As mentioned above, elevated temperatures or/and acidic conditions are required for the synthesis of the perimidines. Thus, the reaction between NDA and strongly dehydrating trifluoroacetic anhydride resulted in the formation of 2-trifluoromethylperimidine at low temperature when 10-fold excess of the anhydride was used. If the same reaction was carried out with equimolar amounts of the reagents, the corresponding monoacyl compound was obtained.

Figure 1:
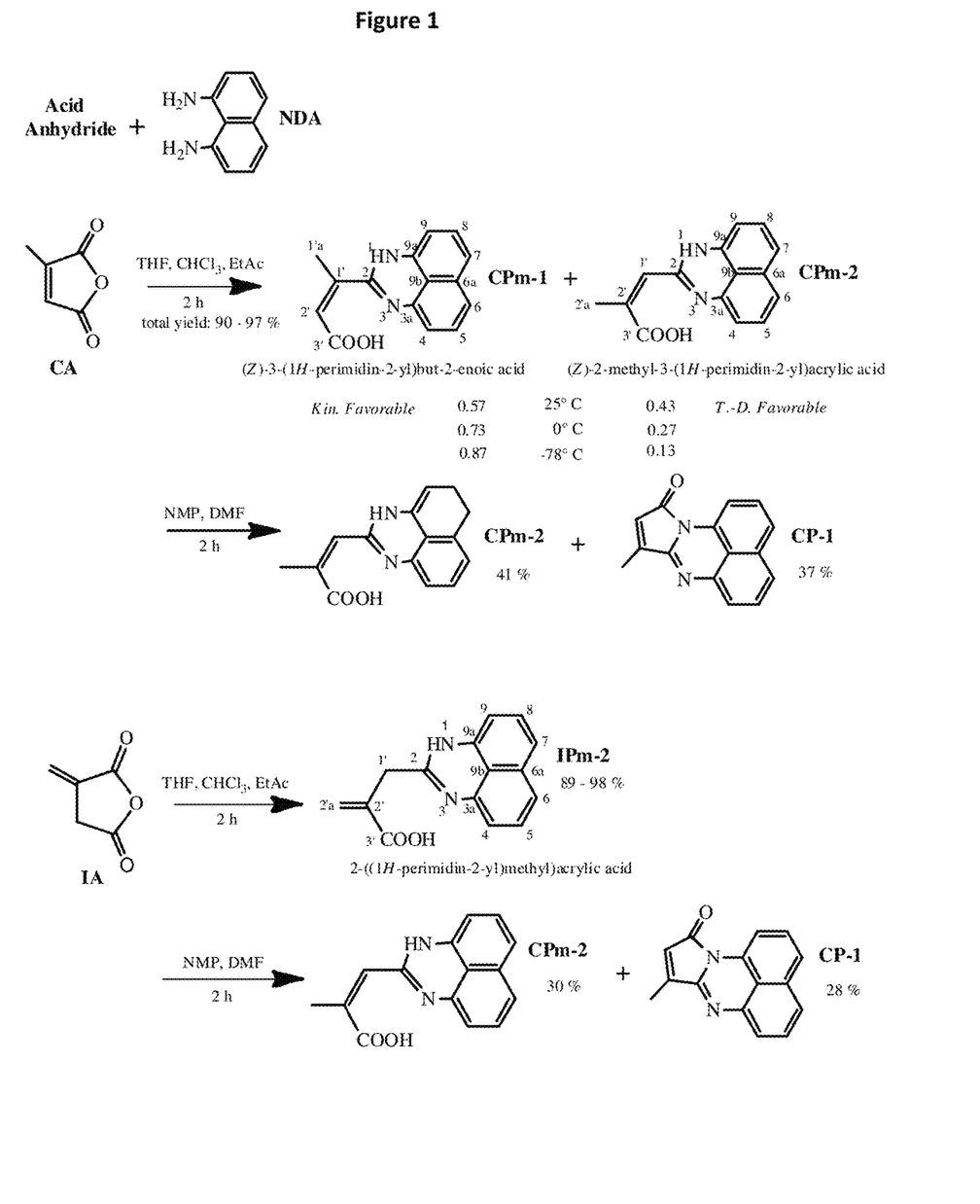
FIG. 1 show a condensation of NDA with IA and CA in different solvents. All yields were determined on isolated products.

Since it is difficult to obtain pure perinone compounds with excellent light emitting properties, the instant invention propose novel conditions for the synthesis of 9-methylene-8H-pyrrolo[1,2-a]perimidin-10(9H)-one by new conditions and reactions of NDA with itaconic acid and its isomer, citraconic anhydride (CA). The results are depicted in FIG. 1.

It has already been shown that the condensation of NDA with itaconic acid in the presence of dehydrating acetic anhydride/pyridine mixture resulted in two isomeric forms of citraco-perinone, CP-1 and CP-2, but not in the desirable 9-methylene-8H-pyrrolo[1,2-a]perimidin-10(9H)-one (Vargas Alfredo N.; Likhatchev D.; Barrientes Ramirez S.; Revilla Vazquez J.; Cedillo Valverde G.; Alexandrova L. Polymer. 2008, 49, 3654-62). Therefore, it is worthy to note that only under very specific conditions, 9-methylene-8H-pyrrolo[1,2-a]perimidin-10(9H)-one is obtainable in exclusive form and with the desired luminescence properties. Analyzing the reactions step by step we have found that the perimidine framework is readily formed in quantitative yields in low polar solvents or under interfacial conditions (CHCl$_3$/H$_2$O) with both, IA and CA, anhydrides without any heating or dehydrating agent added. The perimidines precipitated from the reaction mixture as pale-yellow (IPm) or radish (CPm) powder in the temperature range from −70 to 25° C.; no monoacylated derivatives have been isolated even at −70° C. Both compounds were poorly soluble even in such organic solvents as dimethylformamide (DMF), N-methyl-2-pyrrolidone (NMP) and di-methyl-sulfoxide (DMSO). The $^1$H and $^{13}$C NMR spectra of the product of the condensation with IA were quite simple and resemble those of 2-substituted H-perimidines with the characteristically upfield shifted H4 and H9 protons. As a consequence of the degenerate tautomerism the aromatic carbons and protons in positions 4 and 9, 5 and 8, 6 and 7 become equivalent. Thus, based on NMR data together with results of mass analysis and IR spectrum the product was identified as 2-acrylic acid perimidine (IPm-2) and it was the only reaction product. The condensation of the isomeric CA under the same conditions resulted in two perimidines differing by the position of the methyl group either at 1' (CPm-1) or 2' (CPm-2) carbon atom, similar to the perinone isomerism (CP-1 and CP-2) previously reported. The isomers were formed almost in equal proportion at room temperature, the CPm-1:CPm-2 molar ratio=0.57:0.43, independently on the solvent, but the amount of CPm-1 isomer increased with increasing temperature. For example, the reaction at 0° C. afforded the mixture with CPm-1:CPm-2=0.73:0.27 molar ratio, while at −70° C. the molar fraction of CPm-1 practically reached 90%. Such temperature dependence suggested that the isomer CPm-1 is a kinetically favorable product and CPm-2 is thermodynamically favorable.

When the same reaction between NDA and the anhydrides, both IA and CA, was carried out in polar NMP or DMF two fused heterocycles resulted from the first (perimidine) and secondary (perinone) cyclizations were obtained in quite similar yields. The perimidines were separated by simple filtration from the reaction mixture; and the perinones were isolated by the precipitation of the dark red mother liquid in cold water. Only citraco-forms were obtained from IA meaning that polarity of the solvent may even be more important factor than the amine basicity for the itaco-citraco isomerization as generally assumed. Interestingly, that only one isomeric form of each products, namely CPm-2 and CP-1, were obtained under these conditions in slightly higher yields for CA than for IA. This coincides with our conclusion on a higher thermodynamic stability of CPm-2 isomer, meanwhile less stable CPm-1 undergoes further dehydration affording the CP-1 perinone. Worthy noting that cyclization of CPm-1 to CP-1 took place even in the solid state during the storage of the product, but the process obviously was much slower. Thus, the secondary cyclodehydration partially proceeded in polar solvents at room temperature without any dehydrating agents. However, the targeting 9-methylene-8H-pyrrolo[1,2-a]perimidin-10(9H)-one could not be obtained under these conditions because of the fast itaco-citraco isomerization occurring even before the first cyclization step.

These data are in good agreement to the results obtained when the cyclization to the perinones was performed in the presence of acetic anhydride/pyridine dehydrating mixture in one stage without isolation of intermediates as shown in Scheme 1. Both CP-1 and CP-2 were obtained in practically equal amounts with only a small excess of CP-1 isomer. The dehydrating mixture was mainly used for the cyclodehydration of the more stable CPm-2.

FIG. 1. One-pot condensation of NDA with IA and CA in polar solvents.

To further characterize the reaction mechanism, the elemental steps of some of the above mentioned transformation have been studied using quantum chemistry tools, in order to evaluate influence of methyl- and methylene substitutors in anhydride on the cyclization reactions. Thus we studied the reaction pathway from the amino acid, as the first intermediate in the reaction between diamine and anhydride, to the corresponding perimidines for non-substituted maleic anhydride (MA), and substituted CA and IA. The attack of nitrogen atom of free amino-group at carbonyl carbon, is the rate determining step for the cyclization. The calculations showed that the Gibbs free energy of activation for formation of CPm-1 is 3.0 kcal/mol lower compared to that for the formation of non-substituted maleic-perimidine. The difference in the activation energies between these very similar compounds is related to the higher stability of the non-substituted amino acid intermediate because of strong hydrogen bond between amide carbonyl and hydroxyl group. Such conformation cannot be adopted by the methyl-substituted intermediate due to steric hindrance caused by the methyl group. As a result the cyclization of amino acid produced from CA should occur easier.

The cyclodehydration reaction of CPm-1 and CPm-2 leads to the corresponding methyl-10H-pyrrolo[1,2-a]perimidin-10-ones, CP-1 and CP-2. And, again, much easier formation of CP-1 is accounted for the influence of the methyl group. The TS-CP-1 is 2.7 kcal/mol lower in the Gibbs free energy compared to TS-CP-2. This difference can be explained by the repulsion between lone pare of the pyrimidine nitrogen atom and methyl group in TS-CP-1 that facilitates the ring closure. There is no such assistance for the ring closure in TS-CP-2 resulting in the higher activation energy process.

Synthesis of 9-methylene-8H-pyrrolo[1,2-a]perimidin-10(9H)-one (IP)

Figure 2:
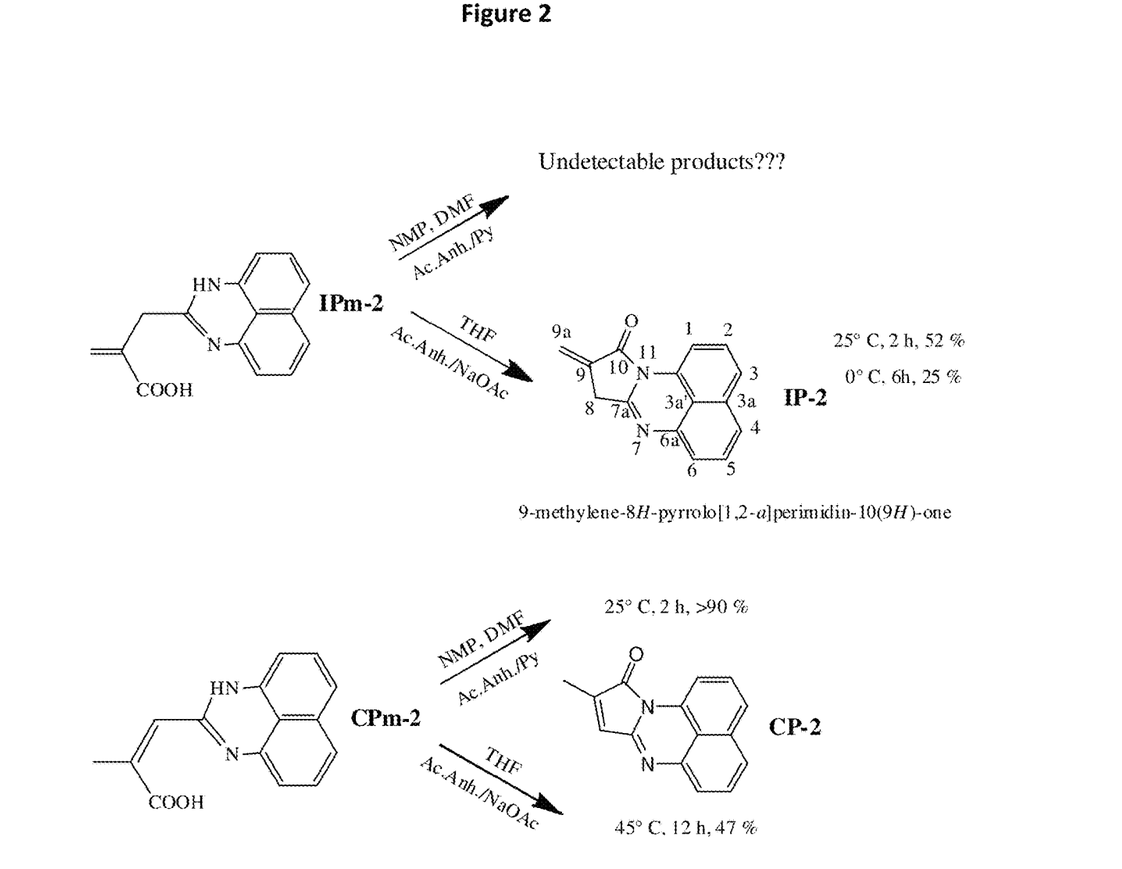
FIG. 2 shows a cyclodehydration of IPm-2 and CPm-2 to the corresponding perinones.

According to the invention, since IPm-2 was the only appropriate intermediate for the following synthesis of the targeting 9-methylene-8H-pyrrolo[1,2-a]perimidin-10(9H)-one search was started for the conditions of its cyclization under which the carbon-carbon ⌊-bond in the anhydride fragment would not be affected. The results are summarized in FIG. 2.

At first we tried to obtain 9-methylene-8H-pyrrolo[1,2-a]perimidin-10(9H)-one skeleton using the traditional acetic anhydride/pyridine dehydrating mixture in amidic solvents because in contrast to itaconic acid, the itaco-perimidine was very stable and according to DSC analysis did not undergo so readily itaco-citraco rearrangement at heating as itaconic acid. The reaction was clearly observed under these conditions, the insoluble IPm-2 disappeared giving dark-red homogenous solution. The product was isolated by filtration after precipitation in cold water in quite a high yield, but we could not determine its structure. The $^1$H NMR spectrum of the dry raw product showed very broadly defined signals, no resonances from methylene- or methyl-protons were observed. Mass analysis showed peaks from various molecular ions, one of them corresponded to mass of the perinone. Attempts to purify by recrystallization or by column chromatography (silica), techniques effectively applied for purification and separation of CPs, were unsuccessful. The product did not form crystals either; CP-2 was isolated as a result of the chromatography but in the minor amount (less than 10%).

For comparison, the cyclization of CPm-2, isomeric form of IPm-2, was also carried out using the same procedure. Similarly, the dark-red homogeneous solution was obtained and the product was separated by precipitation in water. According to the $^1$H NMR analysis it was identified as CP-2 compound of very high purity, no other signals, except those from CP-2, were seen in the spectrum.

Then, by applying other cyclization conditions using any dehydrating agents that does not result in CP rearrangement, such as, but not limited to acetic anhydride/NaOAc dehydrating mixture in neutral organic solvents such as, but not limited to THF, chloroform, ethyl acetate, benzene, toluene, etc., lowering the basicity and polarity of the reaction system. Since the dehydrating capacity of acetic anhydride/NaOAc is weaker, the temperature was increased to 50° C. because at lower temperatures the cyclization proceeded very slow while higher temperatures increased the possibility of itaco-citraco isomerization. Thus, the pale orange-reddish powder was obtained after the appropriate reaction treatment; the $^1$H NMR spectrum of the dry raw product contained, except the aromatic resonances, two intense signals from methylene protons at 5.70 and 6.39 ppm, presumably aroused from the presence of 9-methylene-8H-pyrrolo[1,2-a]perimidin-10(9H)-one compound in important amount. However, the purification was problematic again; after the column separation only citraco-perinone was isolated in very low yield (~8%), but not its itaco-isomer. This made us think that 9-methylene-8H-pyrrolo[1,2-a]perimidin-10(9H)-one was not stable enough under the chromatography conditions and its purification turns out to be a difficult task.

Therefore, the reaction temperature was decreased in order to suppress the side reactions and obtained much more pure IP. And, indeed, practically pure 9-methylene-8H-pyrrolo[1,2-a]perimidin-10(9H)-one (IP-2) was obtained as an orange powder at temperatures from approximately 0° C. to 50° C. after at least 2 h; the yield of 50% was reasonably good but not as high as for the citraco-isomers using solvent mixtures such as, but not limited to acetic anhydride/pyridine, acetic anhydride/NaOAc, trifluoroacetic anhydride, thionyl chloride, polyphosphoric acid, phosphorous pentoxide, phosphoryl chloride, or N,N-dicyclohexylcarbodiimide. Interestingly, that the conversion of IPm-2 into CP-2, which was very fast and efficient using acetic anhydride/pyridine mixture, barely proceeded at room temperature in the presence of acetic anhydride/NaOAc dehydrating agent. The reaction was quite slow even at 45° C. affording less than 50% yield after 12 h. Therefore the substitute plays very important role in mechanism of the cyclization.

Luminescence Properties

Perimidines rarely luminescent on irradiation with UV light, only a few photo-emitting perimidine-based compounds are known to the date. Thus, electronic absorption and emission properties of the perimidines synthesized were studied. Typically, the electronic spectra of perimidine system consists of two highly intense broad absorption bands with maxima at approximately 230 and 330 nm, which are related to the electronic transitions within naphthalene ring and the transfer of the electron pair of the nitrogen to the antibonding π orbital of the naphthalene respectively. Frequently, the third low intense absorption related to charge-transfer between the naphthalene ring (π-donor) and heterocycle (π-acceptor) is also manifested as a shoulder at 400 nm (most perimidines are of bright yellow color) but its position may vary depending on the 2-substituting group. Since CPms and IPm were practically not soluble in organic solvents their spectral characteristic were studied in DMSO but even in this solvent the solubility was very limited. UV-vis spectrum of IPm was quite typical for perimidine framework showing the main absorption at 330 nm with long-wave shoulder at 380 nm explaining its pale-yellow color. Unfortunately, the short-wave band could not be seen because of DMSO absorption in this region. In comparison to the electronic spectrum of IPm, the absorption bands of CPm were red shifted; the main absorption was observed at 350 nm while another band of much lower intensity at 460 nm. Such difference in the spectra between IPm and CPm may be explained by influence of the carbon-carbon double bond in the anhydride fragment on the heterocycle. In CPms the C=C bond enters in conjugation to the C=N bond of the heterocycle, while the C=C bond of IPm is separated by distance of two σ-carbon-carbon bonds from the heterocycle.

UV-vis absorption spectrum of CP also shows two principal bands at 240 and 330 nm, characteristic for perimidine system, together with the long-wave band at approx. 370 nm. However this long wave absorption is much more intense than those typically observed in the spectra of perimidine systems. Intensity of the last absorption band is comparable to the absorption at 330 nm, so they overlap each other resulting in one broad structureless band.

Both itaco-derivatives, IPm and IP, fluorescence though intensity of the fluorescence was very low for IPm. CPms do not show any notable luminescence that coincides with the observation for the completely cyclized CPs. On the contrary, fluorescence of 9-methylene-8H-pyrrolo[1,2-a]perimidin-10(9H)-one was intense with a quantum yield of about 0.2, the highest value among all the perimidines synthesized. The more important aspect is that 9-methylene-8H-pyrrolo[1,2-a]perimidin-10(9H)-one emits white light with maximum at 560 nm, meaning that the emission is broad and covers practically the whole visible region from 390 to 700 nm. The above is illustrated by results presented in insets (a) and (b) of FIG. 3.

Organic luminescent materials are generally preferred over their inorganic counterparts owing to their low cost, solution processability, flexibility and etc. That is why they have found wider applications in the field of artificial lighting, display systems and fluorescence bio-material tools. Current trends in artificial lighting have boosted the demand for white organic light-emitting materials, because in most cases, white-light emitting diodes are made of combination of individual compounds emitting in red, green and blue area of spectrum. Although considerable progress has been made in this field, development of purely organic white-light emitting materials of simple structure was an urgent necessity. The compound 9-methylene-8H-pyrrolo[1,2-a]perimidin-10(9H)-one of the instant invention solves said problem since it displays luminescence in almost all the visible spectra, thus being a white emitting material.

According to the present invention, an organic luminescent material comprising 9-methylene-8H-pyrrolo[1,2-a]perimidin-10(9H)-one and an organic monomer selected from the group comprising styrene, vinyl, acrylate and/or methacrylate that can be polymerized via ionic or radical mechanisms. The competitive advantage of such material is that emits white light without the need of combining individual compounds emitting red, green and blue area of spectrum. Thus, 9-methylene-8H-pyrrolo[1,2-a]perimidin-10(9H)-one is a very promising molecule from this point of view. Since, very frequently the generation of white-light is limited to solution state, 9-methylene-8H-pyrrolo[1,2-a]perimidin-10(9H)-one was co-polymerized with several organic monomers selected, but not limited from the group comprising vinyl, acrylate and/or methacrylate that can be polymerized via ionic or radical mechanisms.

EXAMPLE 1 COPOLYMERIZATION OF 9-METHYLENE-8H-PYRROLO[1,2-A]PERIMIDIN-10(9H)-ONE WITH METHYL METHACRYLATE (MMA) AND STYRENE (St)

Figure 3:
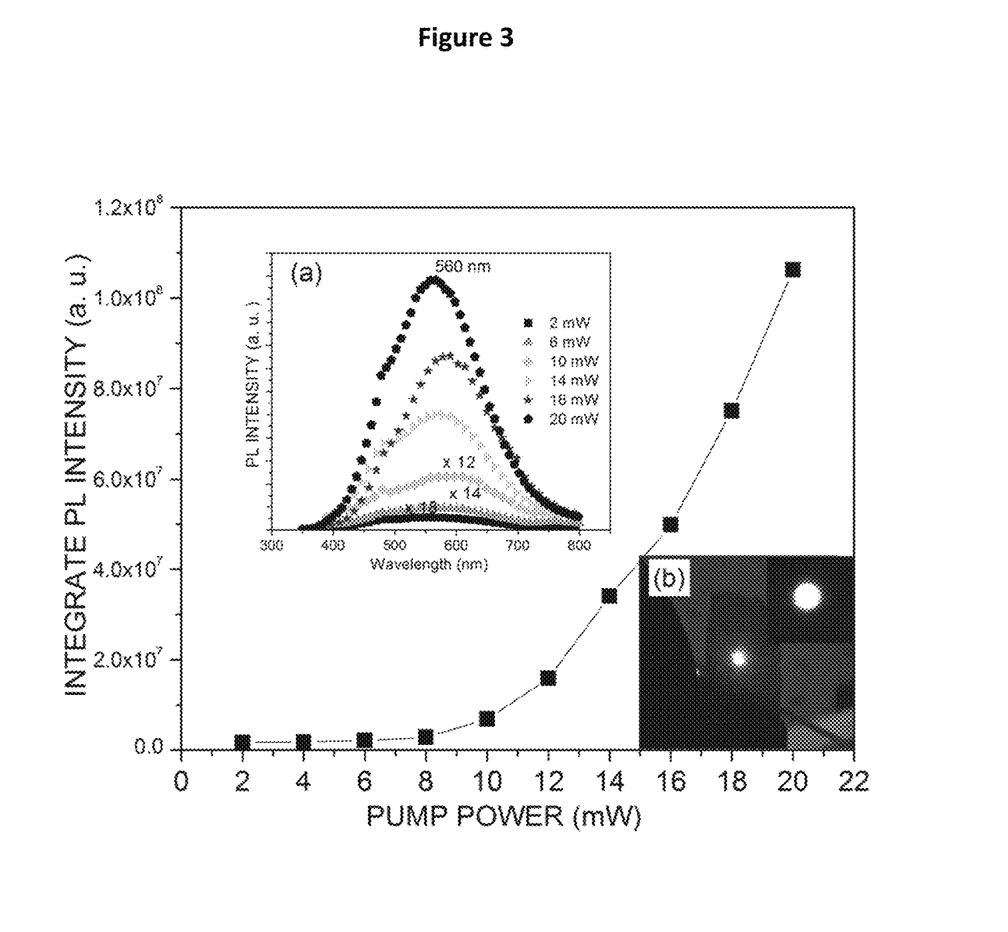
FIG. 3 shows the exponential tendency of the integrate photoluminescence (PL) intensity of poly(MMA-co-IP) film, containing 3 mol % of 9-methylene-8H-pyrrolo[1,2-a]perimidin-10(9H)-one, with respect to the laser power. Insets show (a) the whole PL spectrum and (b) the intense spot emission of the copolymer.

As a non-limiting example, 9-methylene-8H-pyrrolo[1,2-a]perimidin-10(9H)-one can be readily copolymerized with Styrene and/or methyl methacrylate via free radical mechanism, or even chemically incorporated into the polymers, keeping the ability to emit white light intensively. FIG. 3 shows the features of photoluminescence of the copolymer of MMA with 9-methylene-8H-pyrrolo[1,2-a]perimidin-10 (9H)-one (3 mol. %); the emission spectrum of the copolymer and the picture of the emitting sample are given as insets (a) and (b) correspondingly. The emission spectrum of poly(St-co-IP) looked very similar. Additionally, the influence of laser power on the luminescence intensity of the copolymers has been investigated at room temperature. The data is presented in FIG. 3 as a plot of the integrated photoluminescence intensity vs pump power. Pump power has been varied from 2 mW until 20 mW with the step of 2 mW. It is important to note that there is an exponential increase of the integrated luminescence as a function of laser power, which clearly demonstrates a tendency to optical gain of this material.

In conclusion, the reaction between NDA and asymmetric IA and CA resulted in a formation of the 2-substituted perimidines in quantitative yields at low temperature without any dehydrating agent. The solvent nature and substituent group had an important effect on the structure of the product. The efficient route for synthesis of the targeting 9-methylene-8H-pyrrolo[1,2-a]perimidin-10(9H)-one molecule has been obtained. The molecule has several novel and inventive specific electronic features differed it from other perimidines, but importantly, turned out to be luminescent with the broad emission spectrum covering the whole visible region. Additionally, 9-methylene-8H-pyrrolo[1,2-a]perimidin-10(9H)-one is readily copolymerizable with organic monomers maintaining its ability to emit white light intensively.

EXAMPLE 2. SYNTHESIS OF THE COMPOUNDS OF THE INVENTION

General Procedure

Starting materials, reagents and solvents were supplied by Aldrich. 1,8-diaminonaphtelene (NDA) was recrystallized from ethanol, methyl methacrylate (MMA) and styrene (St) were passed through a column filled with neutral alumina. All other chemicals were used as received. Thermal analysis were performed on TA Instruments Thermogravimetric Analyzer, Model Q50001R, and TA Instruments Differential Scanning calorimeter, Model DSQC 2000 at a heating rate of 20° C./min. UV-vis spectra were recorded on a Varian Cary 400 UV-vis spectrophotometer. Fluoresce spectra in solutions were recorded on a Perkin-Elmer LS50B fluorescent spectrometer with Rhodamin 6G as a standard. Photoluminescence spectra of the copolymer samples were obtained using a Kimmon Koha He—Cd laser with $\lambda_{exit}$=325 nm and output power was varied from 2 mW to 20 mW, at room temperature. The sample emission was focused into an Acton SpectraPro 2500i spectrograph and detected by a photomultiplier tube. All the spectra were corrected taking into account the spectral response of the system. Infrared spectra were recorded on a Bruker Alpha-p ATR. Proton and carbon nuclear magnetic resonance (NMR) spectra were obtained using either a VARIAN$^{unity}$ INOVA 500 MHz spectrometer, Bruker Avance III 400 MHz spectrometer. Spectra were acquired in CDCl$_3$ for perinone and DMSO-d6 for perimidines. The peak due to residual CHCl$_3$ (7.26 ppm for $^1$H and 77.23 ppm for $^{13}$C) and the peak due to residual DMSO-d6 (2.54 ppm for $^1$H and 40.45 ppm for $^{13}$C) were used as the internal references. Coupling constant (J) values were given in Hertz, and multiplicity was defined as follows: br=broad, s=singlet, d=doublet, dd=double of doublets, ddd=doublet of doublet doublets, dt=doublet of triplets, t=triplet, td=triplet of doublets, q=quartet, qd=quartet of doublets and m=multiplet. For detailed peak assignments DEPT 90, Dept 135 and 2D spectra were run ($^1$H—$^1$H COSY, HSQC, HMBC). MS were performed with a Jeol, The AccuTOF JMS-T100LC with an IonSense Direct Analysis Real Time (DART), and an Bruker Daltonics, Esquince 6000 LC-Ion trap.

Synthesis of 2-Substituted H-Perimidines

The perimidines were synthesized via condensation of NDA with the corresponding anhydride taken in equimolar amounts. Most of the reactions was carried out at room temperature, but several condensations in CHCl$_3$ were conducted at −78° C. (acetone/dry ice cooling bath), −10° C. (ice/NaCl cooling bath) and 0° C. The details are described below. All the structures synthesized were characterized by NMR ($^1$H and $^{13}$C), FTIR, UV-vis and mass-spectroscopies and thermal analysis. The yields were determined on isolated products.

Itacoperimide (IPm, IUPAC Name 3-(1H-perimidin-2-yl)but-3-enoic Acid)

Itaconic anhydride (1 g, 0.004 mol) was added to a solution of NDA (0.6328 g, 0.004 mol) in 50 mL of chloroform, THF or ethyl acetate and the reaction mixture was stirred for 2 h. A pale yellow powder precipitated from the reaction mixture was filtered off, than washed with ethanol (200 ml) at continuous stirring for another 1 h in order to remove the unreacted residues, then filtrated off again and dried in vacuum to a constant weight. The yields were 98% in CHCl$_3$ and 89% in THF, and EtAc at room temperature. Slightly lower yield of 92% in CHCl$_3$ was obtained at −78° C.; m.p.=215° C.; IR (ATR): 2100-3100 (hydrogen bonds), 1657 (C═O), 1548 (C—N) cm$^{-1}$; $^1$H NMR (400 MHz, DMSO, δ, ppm): 3.24 (s, 2H)(1'), 5.76 (d, J=1.4 Hz, 1H)(2a'), 6.16 (d, J=1.4 Hz, 1H)(2a'), 6.37 (dd, J=7.4, 0.9 Hz, 2H)(4 and 9), 6.97 (dd, J=8.4, 0.9 Hz, 2H)(6 and 7), 7.08 (dd, J=8.3, 7.4 Hz, 2H)(5 and 8); $^{13}$C NMR (101 MHz, DMSO, δ, ppm): 167.55 (quart)(3'), 155.28 (quart)(2), 141.57 (3a and 9a)(quart), 136.31 (quart), 135.08 (quart) (6a), 128.20 (tert)(5 and 8), 126.91 (sec)(2a'), 121.38 (quart) (9b), 118.10 (tert)(6 and 7), 107.34 (tert)(4 and 9), 37.13 (sec)(1');); MS (ESI$^+$) m/z [M+H]$^+$=253.

Citracoperimides (CPms, IUPAC Names (E)-2-methyl-3-(1H-perimidin-2-yl)acrylic Acid (CPm-1) and (E)-3-(1H-perimidin-2-yl)but-2-enoic Acid (CPm-2)

These perimidines were obtained analogously but using citraconic anhydride. In difference to IPm the product was of pale reddish color. The total yields were 97% in CHCl3 and 90% in THF, and EtAc; m.p.=221.5° C.; IR (ATR): 2200-3048 (hydrogen bonds), 1651 (C=O), 1587 (C—N) cm$^{-1}$; $^1$H NMR (400 MHz, DMSO, δ, ppm) for CPm-1: $^1$H NMR (300 MHz, DMSO, δ, ppm): 2.11 (s, 3H)(1a'), 6.01 (s, 1H)(2'), 6.42 (d, J=7.2 Hz, 2H)(4 and 9), 7.02 (d, J=8.3 Hz, 2H)(6 and 7), 7.12 (dd, J=7.2 Hz, 2H)(5 and 8) and for CPm-2:): 2.07 (d, J=1.4 Hz, 3H)(2a'), 6.26 (d, J=1.4 Hz, 1H)(1'), 6.47 (dd, J=7.1, 1.0 Hz, 2H)(4 and 9), 7.13 (dd, J=8.4, 0.9 Hz, 2H)(6 and 7), 7.19 (dd, J=8.3, 7.2 Hz, 2H)(5 and 8); $^{13}$C NMR (101 MHz, DMSO, δ, ppm) for CPm-1: 165.14 (quart)(3'), 154.76 (quart)(2), 145.45 (quart)(1'), 140.92 (quart)(3a and 9a), 134.87 (quart)(6a), 127.92 (tert)(5 and 8), 122.61 (tert)(2'), 121.5 (quart)(9b), 118.07 (tert)(6 and 7), 107.35 (tert)(4 and 9), 21.98 (CH$_3$)(1a') and for CPm-2: 166.93 (quart)(3'), 151.80 (quart)(2), 146.78 (quart)(2'), 137.93 (quart)(3a and 9a), 134.94 (quart)(6a), 128.64 (tert)(5 and 8), 122.71 (tert)(1'), 121.23 (quart)(9b), 119.91 (tert)(6 and 7), 107.55 (tert)(4 and 9), 24.26 (CH$_3$)(2a'); MS (ESI$^+$) m/z [M+H]$^+$=253.

CPm-2

This compound was obtained as a reddish precipitator in the reaction of NDA with CA or IA using the same procedure as described in section 2.2 but in polar amidic solvents, DMF or NMP. Analogously the precipitator was washed with ethanol and dried. The yields were 40 and 30% for CA and IA respectively. Precipitation in cold water of the mother liquid resulted in CP-1.

Synthesis of the Luminescence Compound 9-methylene-8H-pyrrolo[1,2-a]perimidin-10(9H)-one (IP)

IPm (1 g, 0.004 mol) was added to 35 ml of THF with sodium acetate (0.278 g, 0.001 mol), then acetic anhydride (5 mL, 0.053 mol) was added and the mixture was stirred for 2 h at room temperature. Then unreacted IPm was filtered off and the mother liquid was poured in water (200 ml) and neutralized with sodium bicarbonate. The orange precipitator was filtered off, washed with water and dried in vacuum to a constant weight. The yield was 45-50%; m.p.≈145° C. (the endotherm overlaps with the exotherm of isomerization); IR (ATR):): 1739 (C=O), 1663 (C=N), 1583 (heteroc. syst.), 1403 (C—N) cm$^{-1}$. The general formula of the compound is:

comprising the following spectroscopic parameters: $^1$H NMR (500 MHz, CDCl$_3$, δ ppm): 3.55 (t, J=2.5 Hz, 2H)(8), 5.70 (t, J=2.3 Hz, 1H)(9a), 6.39 (t, J=2.7 Hz, 1H)(9a), 7.04 (dd, J=7.1, 1.1 Hz, 1H)(6), 7.32 (td, J=8.1, 2.3 Hz, 2H)(2 and 5), 7.36 (dd, J=8.3, 1.0 Hz, 1H)(4), 7.44 (dd, J=8.3, 0.6 Hz, 1H)(3), 8.31 (dd, J=7.7, 0.8 Hz, 1H)(1). $^{13}$C NMR (126 MHz, CDCl$_3$ δ, ppm): 166.09 (quart)(10), 153.53 (quart)(7a), 139.43 (quart)(6a), 134.17 (quart)(3a), 133.06 (quart)(9), 131.80 (quart)(11a), 128.07 (tert)(5), 127.26 (tert)(2), 123.91 (tert)(3), 123.56 (tert)(4), 120.87 (sec)(9a), 119.84 (quart)(3a'), 118.79 (tert)(6), 109.77 (tert)(1), 31.15 (sec)(8); MS (DART) m/z=234.

Said compound has the luminescence emitting properties as above discussed.

Copolymerization of 9-methylene-8H-pyrrolo[1,2-a]perimidin-10(9H)-one (IP) with Methyl Methacrylate and/or Styrene The initial monomer feeds containing from 0.01 to 30 mol. % of IP were used for co-polymerizations. The polymerizations were carried out in bulk under N$_2$ using AlBN (0.05 M) as radical initiator at 80° C. for MMA and 110° C. for St. The monomer conversion was determined gravimetrically. The copolymerizations with MMA were stopped after 50 min by cooling and the conversions of 32% (IP/MMA=1/99) and 24% (IP/MMA=3.2/96.8) were obtained. For comparison, pure MMA was polymerized with 80% conversion in 20 min under these conditions. The copolymerizations with St were stopped after 30 min, that resulted in conversions of 44% and 20% for IP/St=1/99 and IP/St=3/97 feeding compositions correspondingly. The homopolymerization of St afforded 55% conversion in 30 min using these conditions. Thus the tendency of decreasing the polymerization rate with increase of the perinone concentration, which observed for other perinones, also maintained for IP. In order to remove the unreacted IP the copolymers obtained were dissolved in THF and then precipitated in methanol. The procedure was repeated several times till no absorption bands related to IP were observed in UV-vis spectrum of the methanol used for the precipitation. The amount of IP in the co-polymers was evaluated using the absorption at 380 nm in the electronic spectra. Therefore, a white luminescent material comprising the luminescent perinone compound of formula:

copolymerized with an organic monomer, is obtained.

What is claimed is:
1. A luminescent perinone compound of formula:

2. A process for preparing a compound of formula:

comprising the steps of: reacting naphthalene-1,8-diamine with itaconic acid and citraconic anhydride.

3. The process according to claim 2, further comprising the step of reacting the itaconic acid and the citraconic anhydride with polar compounds.

4. The process according to claim 3, wherein said polar compounds comprise tetrahydrofuran, chloroform, ethyl acetate, N-methyl-2-pyrrolidone, and dimethylformamide.

5. The process according to claim 3, wherein the mixture is filtered and further precipitated.

6. The process according to claim 5, wherein the precipitate further reacts with organic solvents.

7. The process according to claim 6, wherein said organic solvents are tetrahydrofuran, acetic anhydride and sodium acetate.

* * * * *